United States Patent [19]

Koehler et al.

[11] Patent Number: 4,900,825
[45] Date of Patent: Feb. 13, 1990

[54] PREPARATION OF 4-NITRO-5-IMIDAZOLYL ETHERS AND THIOETHERS

[75] Inventors: Hermann Koehler, Beindersheim; Toni Dockner, Meckenheim, both of Fed. Rep. of Germany

[73] Assignee: BASF Aktiengesellschaft, Ludwigshafen, Fed. Rep. of Germany

[21] Appl. No.: 201,051

[22] Filed: Jun. 1, 1988

[30] Foreign Application Priority Data

Jun. 5, 1987 [DE] Fed. Rep. of Germany ....... 3718898
Sep. 3, 1987 [DE] Fed. Rep. of Germany ....... 3729406

[51] Int. Cl.$^4$ ................. C07D 279/00; C07D 401/00; C07D 261/04; C07D 417/00
[52] U.S. Cl. ..................................... 544/276; 544/327; 544/331; 544/328; 546/177; 546/210; 546/278; 548/197; 548/214; 548/338; 548/339; 548/340; 548/336
[58] Field of Search ............... 548/338, 339, 340, 336, 548/197, 214, 233, 245, 246; 544/3, 55, 54, 60, 63, 129, 238, 331, 327, 328, 370, 405, 265, 276; 546/210, 278

[56] References Cited

U.S. PATENT DOCUMENTS 3,056,785 10/1962 Hitchings et al. .................. 548/338
3,862,061 1/1975 Elion et al. ......................... 548/338

FOREIGN PATENT DOCUMENTS 220961 10/1985 Fed. Rep. of Germany ...... 548/338

OTHER PUBLICATIONS

P. M. Kochergin et al., Chemistry of Heterocyclic Compounds, (1971), p. 648.
Arya et al., Indian Journal of Chemistry, 21 B, (1982), p. 1115.
Liebig's Annalen der Chemie, 184, (1877), p. 51.
L. L. Bennett, Jr., and H. T. Baker, J. American Chem. Soc., 79, (1957), p. 2188.
Chemical Abstracts, 96; 104146a, (1981).

Chemical Abstracts, 64; 735a, (1966), (corresponds to Med. Prom. SSSR, 19, (1965), p. 6).
S. S. Novikov et al., Chem. Heterocyclic Compounds, (1970), p. 465.
Baloniak et al., Chem. Abstr., vol. 107, (1987), 217370h.
Suwinski et al., Chem. Abstr., vol. 107, (1987), 77701q.
Ichino et al., Chem. Abstr., vol. 85, (1976), 5680m.

Primary Examiner—Mary C. Lee
Assistant Examiner—Robert C. Whittenbaugh
Attorney, Agent, or Firm—John H. Shurtleff

[57] ABSTRACT

4-Nitro-5-imidazolyl ethers and thioethers of the formula I

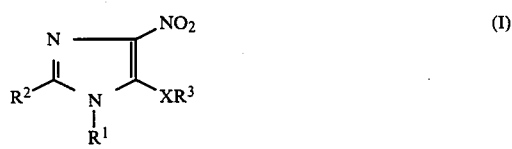

where $R^1$ is alkyl, alkoxyalkyl, cycloalkyl, aryl, aralkyl or alkylaryl, $R^2$ is hydrogen, alkyl, cycloalkyl, aryl, aralkyl or alkylaryl, $R^3$ is alkyl, cycloalkyl, aryl, aralkyl, alkylaryl or a heterocyclic or heteroaromatic radical or a counter-ion of the corresponding alcoholate or thiolate or, where X is sulfur, $R^3$ is hydrogen, and X is oxygen or sulfur, and the stated organic radicals may furthermore carry substituents which are inert under the reaction conditions, are prepared by reacting a dinitroimidazole of the formula II

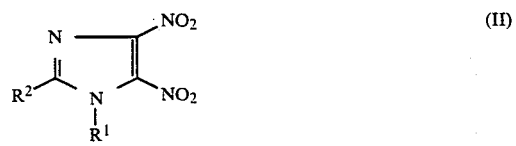

with an alcohol or thiol of the formula III

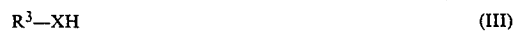

in a solvent or diluent at a pH of the from 4 to 16.

10 Claims, No Drawings

PREPARATION OF 4-NITRO-5-IMIDAZOLYL ETHERS AND THIOETHERS

The present invention relates to a process for the preparation of 4-nitro-5-imidazolyl ethers and thioethers.

P. M. Kochergin et al., Chemistry of Heterocyclic Compounds 1971, 648 and V. P. Arya et al., Indian Journal of Chemistry 21 B (1982), 1115 disclose that ethers of the formula I where $R^1$ is $CH_3$ and $R^2$ is H are obtained by reacting 1-methyl-4-nitro-5-chloroimidazole with an oxygen compound.

1-methyl-4-nitro-5-chloroimidazole is obtainable in only a poor yield by reacting N,N'-dimethyloxalicaciddiamide with phosphorus pentachloride and then nitrating the resulting 1-methyl-5-chloroimidazole (O. Wallach, Liebigs Annalen der Chemie 184 (1877), 51).

L.L. Bennett Jr. and H.T. Baker, J. Amer. Chem. Soc. 79 (1957), 2188 disclose that thioethers of the formula I where $R^1$ is $CH_3$ and $R^2$ is H are obtained by reacting 1-methyl-4-nitro-5-chloroimidazole with a mercaptan in strongly alkaline solution. If the reaction of this chloroimidazole or of the 2-methylhomolog is carried out in the presence of 20% strength sodium carbonate solution, it is possible to use different thiols which are alkyl-substituted, aryl-substituted or substituted by a heterocyclic radical, as described in Chemical Abstracts 96, 104146a, 1981.

These compounds can also be prepared by reacting the sodium thiolate of 1-methyl-4-nitro-5-mercaptoimidazole with an alkyl halide (P. M. Kochergin and I. S. Shmidt, Med. Prom. SSSR 19 (1965), 6; cf. CA 64 735 a (1966)), and the thiolate in turn can be obtained from 1-methyl-4-nitro-5-chloroimidazole (L. L. Bennett Jr. and H. T. Baker, loc. cit).

A disadvantage of the processes described is the small range of applications.

It is an object of the present invention to provide a novel and improved process for the preparation of 4-nitro-5-imidazolyl ethers and thioethers of the formula I and to remedy the disadvantages of the known processes.

We have found that this object is achieved by a novel and improved process for the preparation of 4-nitro-5-imidazolyl ethers and thioethers of the general formula I

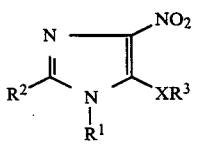

where $R^1$ is alkyl, alkoxyalkyl, cycloalkyl, aryl, aralkyl or alkylaryl, $R^2$ is hydrogen, alkyl, cycloalkyl, aryl, aralkyl or alkylaryl, $R^3$ is alkyl, cycloalkyl, aryl, aralkyl, alkylaryl or a heterocyclic or heteroaromatic radical or a counter-ion of the corresponding alcoholate or thiolate or, if X is sulfur, $R^3$ is hydrogen, and X is oxygen or sulfur, and the stated organic radicals may furthermore carry substituents which are inert under the reaction conditions, wherein they are advantageously obtained if a dinitroimidazole of the formula II

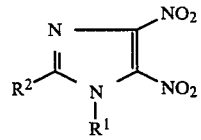

is reacted with an alcohol or thiol of the formula III $$R^3{-}XH \qquad (III)$$

in a solvent or diluent at a pH of 4 to 16.

The success of the novel process is surprising particularly in view of the fact that only the nitro group in the 5-position of the imidazole II is selectively exchanged.

The preparation of compounds of the formula II has been described (S. S. Novikov et al., Chem. Heterocyclic Compds. 1970, 465; cf. CA 73, 66491 z (1970)). A large number of different substituted compounds of the formula II are obtainable by the process described there.

$R^1$ may be, for example, alkyl, alkoxyalkyl, cycloalkyl, aryl, aralkyl or alkylaryl. Alkyl is, for example, straight-chain or branched radicals of 1 to 18, in particular 1 to 8, carbon atoms, such as methyl, ethyl, propyl, isopropyl, n-butyl, sec-butyl, tert-butyl, pentyl, hexyl, heptyl or octyl. Alkoxyalkyl has, for example, a total of 2 to 8 carbon atoms, eg. $C_1$–$C_4$-alkoxymethyl, methoxyethyl or ethoxyethyl. Cycloalkyl is, for example, $C_5$–$C_8$-cycloalkyl, in particular cyclopentyl or cyclohexyl. Aryl is, for example, phenyl or naphthyl, unsubstituted or substituted by inert groups such as $C_1$–$C_4$-alkyl, $C_1$–$C_4$-alkoxy, halogen, such as fluorine, chlorine or bromine, haloalkyl, such as trifluoromethyl, difluoromethyl or dichloromethyl, or $C_1$–$C_4$-alkoxymethyl. Aralkyl and alkylaryl are in particular radicals of 7 to 12 carbon atoms, such as tolyl, xylyl, phenylethyl or benzyl, which may be substituted like the aryl radicals.

$R^2$ may have the meanings of $R^1$ and may furthermore be hydrogen. The organic radicals $R^1$ and/or $R^2$ may furthermore carry substituents which are inert under the reaction conditions, such as $C_1$–$C_4$-alkyl, alkoxy or halogen, such as fluorine, chlorine or bromine. $R^2$ is preferably hydrogen, $C_1$–$C_4$-alkyl, such as methyl, ethyl or isopropyl, alkoxymethyl, such as methoxymethyl, phenylethyl or benzyl.

The alcohols and thiols of the formula III are known and can be prepared by processes known from the literature.

For example, $R^3$ may be hydrogen, alkyl, alkoxyalkyl, cycloalkyl, aryl, aralkyl or alkylaryl, ie. may have the meanings stated for $R^1$, and the said radicals may furthermore be substituted by inert groups, such as low molecular weight alkyl, haloalkyl, alkoxy or dialkylamino groups or by halogen, such as fluorine, chlorine or bromine. The inert substituents are advantageously of 1 to 6 carbon atoms. $R^3$ is, for example, hydrogen, $C_1$–$C_4$-alkyl, such as methyl, ethyl, propyl, isopropyl or butyl, aryl or aralkyl, such as phenyl, 1-naphthyl, 2-naphthyl, 4-chlorophenyl, 2,4-dichlorophenyl, 2-bromophenyl, 4-methoxyphenyl, 3-(trifluoromethyl)-phenyl, 3-(difluoromethyl)-phenyl, benzyl or 4-chlorobenzyl.

$R^3$ may furthermore be a heterocyclic or heteroaromatic radical, suitable heteroatoms being oxygen and sulfur and in particular nitrogen. The heteroaromatic radicals advantageously have 5 or 6 ring members and 1 or 2 heteroatoms and may be fused with a further 5-membered or 6-membered ring which is, for example, aromatic or heteroaromatic. Examples are the following radicals: 3-pyridyl, 2-pyridyl, 2-pyrimidyl, 8-quinolyl, 2-imidazolyl, 2-thiazolyl and 6-purinyl. Heterocyclic radicals are, for example, heterocyclic radicals which are saturated or contain double bonds and possess 1 or 2 heteroatoms, such as 3-tetrahydropyridyl or 2-thiazolyl.

Where strong bases are used and the reaction is carried out in alkaline medium, $R^3$ may furthermore be the counter-ion of the corresponding alcoholate or thiolate. Depending on the base used, examples of counter-ions are alkali metal and alkaline earth metal ions and ammonium ions, in particular sodium, potassium, calcium, ammonium or trialkylammonium.

In the novel process, 4-nitro-5-imidazolyl ethers and thioethers of the structure I can be obtained in a simple manner if a dinitroimidazole II is reacted with a compound III or, where $R^3$ is H, with hydrogen sulfide in a solvent or diluent at a pH of 4 or higher, eg. from 4 to 16, in particular from 6 to 14, particularly advantageously from 8 to 14.

Particularly suitable solvents or diluents are water and/or water-miscible inert organic solvents. Examples of suitable organic solvents are low molecular weight alcohols, glycols and glycol derivatives, such as ethylene glycol, methylglycol and ethylglycol, and amides, such as dimethylformamide. Preferred solvents are water and/ or $C_1$-$C_4$-alcohols, eg. methanol, ethanol, propanol, isopropanol, butanol and isobutanol.

The pH of the reaction mixture is generally adjusted by adding a base. Examples of suitable bases are hydroxides, carbonates or bicarbonates of alkali or alkaline earth metals, ammonia or organic nitrogen compounds, such as tertiary amines, eg. trimethyl-, triethyl-, tripropyl- or tributylamine, N,N-dimethylaniline or pyridine. Carbonates, such as potassium carbonate or sodium carbonate, trialkylamines or ammonia are preferably used. For the preparation of thiolates, strong bases, such as sodium hydroxide, potassium hydroxide, calcium hydroxide or amines, are particularly chosen.

The amount of base is not particularly critical, and the base may be used in an amount of, for example, from 0.1 to 100, advantageously from 1 to 20, moles per mole of dinitroimidazole II.

The molar ratio of the compound III, based on the dinitroimidazole II, is expediently from 1 to 5, advantageously from 1 to 3, particularly advantageously from 1 to 1.2.

The reaction can be carried out under extremely mild conditions. Temperatures of from 0° to 150° C. are sufficient. The reaction is preferably carried out at from 20° to 80° C.

The reaction is usually carried out continuously or batchwise under atmospheric pressure in a suitable apparatus. In the case of volatile compounds III, eg. methyl mercaptan, it may be advantageous to carry out the reaction under slightly superatmospheric pressure in a closed apparatus.

The products are isolated and purified in a conventional manner, for example by filtering off the solid products and recrystallizing them from suitable solvents. Where $R^3$ is H, the end product is liberated from the corresponding alcoholate or thiolate by acidification. Frequently, however, the salts themselves, for example the sodium or ammonium salts of the 4-nitro-5-imidazolyl ethers or thioethers, are used directly for further reactions.

The novel procedure gives the 4-nitro-5-imidazolyl ethers and thioethers I in good or very good yields.

4-Nitro-5-imidazolyl ethers and thioethers I are useful intermediates for the preparation of dyes and crop protection agents. The imidazoles I are preferably used for the preparation of pharmacologically active compounds or are themselves active compounds. For example, 6-(1-methyl-4-nitro-5-imidazolyl)-mercaptopurine is an effective immunosuppressant (cf. U.S. Pat. No. 3,056,785).

The Examples which follow illustrate the invention without restricting it.

EXAMPLE 1

Preparation of 1-methyl-4-nitro-5-mercaptophenylimidazole 13.2 g (0.12 mole) of thiophenol were added to a stirred mixture of 17.2 g (0.1 mole) of 1-methyl-4,5-dinitroimidazole, 75 ml of 25% strength $NH_3$ and 75 ml of water, the temperature of the solution increasing from 22° C. to 38° C. Stirring was continued for a further 0.5 hour, after which the precipitated crystals were filtered off and recrystallized from isopropanol.

21.9 g (93%) of 1- methyl-4- nitro-5-mercaptophenylimidazole of melting point 73°–75° C. were obtained.

EXAMPLES 2 TO 9

Preparation of 1-methyl-4-nitroimidazoles having various substituents

The Examples shown in Table A below were carried out similarly to Example 1.

TABLE A

| Example | $R^1$ | $R^2$ | $R^3$ | Yield % based on II | mp. °C. | Elemental analysis C:H:N:S in % |
|---------|-------|-------|-------|---------------------|---------|----------------------------------|
| 2 | $CH_3$ | H | $CH_3-CH_2-CH_2-$ | 65 | 43–44 | |
| 3 | $CH_3$ | H | $CH_3-(CH_2)_{11}-$ | 73 | 86–88 | Found: 58.4:8.7:13.0:9.5 |
| | | | | | | Calc: 58.7:8.9:12.8:9.8 |

TABLE A-continued $$R^2-C(=N-)-N(R^1)-C(=C(NO_2)(NO_2)) + R^3SH \longrightarrow R^2-C(=N-)-N(R^1)-C(=C(NO_2)(SR^3))$$

| Example | $R^1$ | $R^2$ | $R^3$ | Yield % based on II | mp. °C. | Elemental analysis C:H:N:S in % | |
|---|---|---|---|---|---|---|---|
| 4 | $CH_3$ | H | 4-Cl-C$_6$H$_4$- | 78 | 128–129 | Found: | 44.6:3.1:15.3:11.5; Cl: 13.2 |
| | | | | | | Calc: | 44.5:3.0:15.6:11.9; Cl:13.1 |
| 5 | $CH_3$ | H | 2-naphthyl | 67 | 154–156 | Found: | 60,1:3.9:13.7:12.0 |
| | | | | | | Calc: | 58.9:3.9:14.7:11.2 |
| 6 | $CH_3$ | H | 3-pyridyl | 89 | 95–97 | Found: | 44.7:3.1:24.9:12.1 |
| | | | | | | Calc: | 45.8:3.4:23.7:13.6 |
| 7 | $CH_3$ | H | (purinyl) | 96 | 251–253 | | |
| 8 | $CH_3$ | $CH_3$ | C$_6$H$_5$- | 76 | 89–92 | Found: | 52.8:4.6:17.1:12.8 |
| | | | | | | Calc: | 52.9:4.4:16.8:12.9 |
| 9 | $C_6H_5$—$CH_2$ | $CH_3$ | 4-Cl-C$_6$H$_4$- | 90 | 123–125 | Found: | 56.8:4.0:11.6:8.8; Cl: 10.0 |
| | | | | | | Calc: | 56.7:8.9:11.7:8.9; Cl: 9.9 |

EXAMPLE 10

Preparation of 1-methyl-4-nitro-5-mercaptophenylimidazole 69 g of $K_2CO_3$ were added to a stirred suspension of 17.2 g (0.1 mole) of 1- methyl- 4,5-dinitroimidazole in 65 ml of water, followed by 12.1 g (0.11 mole) of thiophenol, the temperature of the solution increasing from 22° C. to 40° C. Stirring was continued for a further hour at this temperature, after which the precipitated crystals were filtered off and recrystallized from isopropanol.

19.3 g (82%) of 1-methyl-4-nitro-5-mercaptophenylimidazole of melting point 73°–76° C. were obtained.

EXAMPLE 11

Preparation of 1-methyl-4-nitro-5-mercaptophenylimidazole 12.1 g (0.11 mole) of thiophenol were added to a stirred suspension of 17.2 g (0.1 mole) of 1-methyl-4,5-dinitroimidazole in 20.2 g of triethylamine and 75 ml of ethanol, the temperature of the solution increasing from 22° C. to 50° C. Stirring was continued for a further 0.5 hour at this temperature, after which 150 ml of isopropanol were added to the solution. The precipitated crystals were filtered off under suction and recrystallized from isopropanol.

20.9 g (89%) of product of melting point 73°–76° C. were obtained.

EXAMPLE 12

Preparation of the ammonium salt of 1-methyl-4-nitro-5-mercaptoimidazole

A gentle stream of $H_2S$ was passed through a stirred mixture of 17.2 g (0.1 mole) of 1-methyl-4,5-dinitroimidazole, 75 ml of 25% strength $NH_3$ and 75 ml of water for 0.25 hour, the temperature of the solution increasing from 21° C. to 55° C. Stirring was continued for a further hour, after which the precipitated crystals were filtered off and recrystallized from methanol.

16.8 g (95%) of the ammonium salt of 1-methyl-4-nitro-5-mercaptoimidazole of melting point 195°–198° C. were obtained.

EXAMPLE 13

Preparation of 1-methyl-4-nitro-5-phenoxyimidazole

A mixture of 17.2 g (0.1 mole) of 1-methyl-4,5-dinitroimidazole, 11.2 g (0.12 mole) of phenol and 4.4 g (0.11 mole) of NaOH in 200 ml of water was stirred for 1 hour at 50° C. Thereafter, the solution was diluted with a further 300 ml of water and was cooled. The precipitated crystals were filtered off under suction and recrystallized from water. 21.0 g (96%) of 1-methyl-4-nitro-5-phenoxyimidazole of melting point 116°–118° C. were obtained.

Elemental analysis: Calculated: C 54.8% H 4.1% N 19.2% O 21.9%; Found: C 54.2% H 4.0% N 18.9% O 22.2%.

EXAMPLES 14 TO 23

The compounds specified in Table B below were prepared according to Example 13:

TABLE B

| Example | $R^1$ | $R^2$ | $R^3$ | Yield | mp. (°C.) | Elemental analysis | |
|---|---|---|---|---|---|---|---|
| 14 | $CH_3-$ | $H-$ | 4-methoxyphenyl | 97% | 119–121 | Calc: | C 53.0: H 4.5: N 16.9: O 25.7 |
| | | | | | | Fnd: | C 52.9: H 4.8: N 17.1: O 25.8 |
| 15 | $CH_3-$ | $H-$ | 4-chlorophenyl | 97% | 116–118 | Calc: | C 47.4: H 3.2: N 16.6: O 18.9: Cl 14.0 |
| | | | | | | Fnd: | C 47.2: H 3.5: N 16.8: O 18.7: Cl 13.7 |
| 16 | $CH_3-$ | $H-$ | 3,4-dichlorophenyl | 67% | 168–171 | Calc: | C 41.7: H 2.5: N 14.6: O 16.7: Cl 24.5 |
| | | | | | | Fnd: | C 41.3: H 2.7: N 15.0: O 16.4: Cl 23.7 |
| 17 | $CH_3-$ | $H-$ | 3,5-dichlorophenyl | 69% | 206–207 | Calc: | C 41.7: H 2.5: N 14.6: O 16.7: Cl 24.5 |
| | | | | | | Fnd: | C 41.3: H 2.5: N 14.7: O 16.4: Cl 24.3 |
| 18 | $CH_3-$ | $H-$ | 3,4-dibromophenyl | 67% | 194–196 | Calc: | C 31.9: H 1.9: N 11.1: O 12.7: Br 42.2 |
| | | | | | | Fnd: | C 32.0: H 1.9: N 11.3: O 12.8: Cl 42.4 |
| 19 | $CH_3-$ | $H-$ | 4-pyridyl | 75% | 241–243 | Calc: | C 49.1: H 3.7: N 25.4: O 21.8 |
| | | | | | | Fnd: | C 48.9: H 4.1: N 25.9: O 21.6 |
| 20 | $CH_3-$ | $H-$ | 8-quinolyl | 97% | 173–175 | Calc: | C 57.8: H 3.7: N 20.7: O 17.8 |
| | | | | | | Fnd: | C 57.6: H 4.2: N 20.9: O 17.5 |
| 21 | $CH_3-$ | $CH-$ | 4-chlorophenyl | 92% | 181–182 | Calc: | C 49.4: H 3.8: N 15.7: O 17.9: Cl 13.2 |
| | | | | | | Fnd: | C 49.2: H 3.8: N 15.6: O 17.5: Cl 13.3 |
| 22 | $CH_3-$ | $CH_3-$ | 8-quinolyl | 90% | 181–182 | Calc: | C 59.2: H 4.3: N 19.7: O 16.9 |
| | | | | | | Fnd: | C 58.9: H 4.3: N 19.3: O 17.0 |
| 23 | $CH_2-$ phenyl | $CH_3-$ | 4-chlorophenyl | 85% | 164–165 | Calc: | C 59.4: H 4.1: N 12.2: O 14.0: Cl 10.3 |
| | | | | | | Fnd: | C 59.4: H 4.3: N 12.1: O 14.4: Cl 10.5 |

EXAMPLE 24

Preparation of 1-methyl-4-nitro-5-methoxyimidazole

A solution of 17.2 g (0.1 mole) of 1-methyl-4,5-dinitroimidazole and 6.0 g (0.11 mole) of sodium methylate in 200 ml of methanol was stirred for 1 hour at 60° C. Thereafter, the solution was evaporated down and the residue was recrystallized from water.

10.0 g (64%) of 1-methyl-4-nitro-5-methoxyimidazole of melting point 140°–141° C. (literature: 134°–135° C.) were obtained.

EXAMPLE 25

Preparation of 1-methyl-4-nitro-5-phenoxyimidazole 9.9 g of 30% strength sodium methylate solution in methanol (corresponding to 0.11 mole of NaOMe) were added to a solution of 11.2 g (0.12 mole) of phenol in 100 ml of dimethylformamide (DMF). The methanol was then distilled off completely at 50° C. under reduced pressure. 17.2 g (0.1 mole) of 1-methyl-4,5-dinitroimidazole were then added to the remaining solution, after which stirring was carried out for 1 hour at 50° C. The mixture was cooled and then diluted with 200 ml of water, and the precipitated crystals were filtered off under suction and recrystallized from water.

18.0 g (82%) of 1-methyl-4-nitro-5-phenoxyimidazole of melting point 115°–118° C. were obtained.

EXAMPLE 26

Preparation of 1-methyl-4-nitro-5-dodecylimidazole 12.3 g (0.11 mole) of potassium tert-butylate were added to a solution of 22.3 g (0.12 mole) of dodecanol in 100 ml of DMF. The tert-butanol was then distilled off completely at 50° C. under reduced pressure. 17.2 g (0.1 mole) of 1-methyl-4,5-dinitroimidazole were added to the remaining solution, after which stirring was carried out for 3 hours at 70° C. Thereafter, the solution was evaporated down and the residue was extracted with hot petroleum ether. The extract was evaporated down and the residue was recrystallized from petroleum ether.

11.0 g (35%) of 1-methyl-4-nitro-5-dodecylimidazole of melting point 56°–59°C. were obtained. Elemental analysis: Calculated: C 61.7 H 9.4 N 13.5 O 15.4; Found: C 61.6 H 8.6 N 13.1 O 15.3.

We claim:

1. A process for the preparation of a 4-nitro-5-imidazolyl ether or thioether of the formula

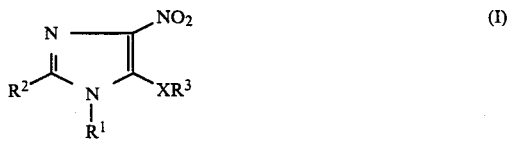

where $R_1$ is $C_1$–$C_{18}$-alkyl, $C_2$–$C_8$-alkoxyalkyl, $C_5$–$C_8$-cycloalkyl, phenyl or naphthyl, unsubstituted or substituted by $C_1$–$C_4$-alkyl, $C_1$–$C_4$-alkoxy, halogen, $C_1$14 $C_4$-haloalkyl or $C_1$–$C_4$-alkoxymethyl, $C_7$–$C_{12}$-aralkyl or $C_7$–$C_{12}$-alkylphenyl, $R^2$ is hydrogen, $C_1$–$C_{18}$-alkyl, $C_5$–$C_8$-cycloalkyl, phenyl or naphthyl, unsubstituted or substituted by $C_1$–$C_4$-alkyl, $C_1$–$C_4$-alkoxy, halogen, $C_1$–$C_4$-haloalkyl or $C_1$–$C_4$-alkoxymethyl, $C_7$–$C_{12}$-aralkyl or $C_7$–$C_{12}$-alkylphenyl, $R^3$ is $C_1$–$C_{18}$-alkyl, $C_2$–$C_8$-alkoxyalkyl, $C_5$–$C_8$-cycloalkyl, phenyl or naphthyl, unsubstituted or substituted by $C_1$–$C_4$-alkyl, $C_1$–$C_4$-alkoxy, halogen, $C_1$–$C_4$-haloalkyl or $C_1$–$C_4$-alkoxymethyl, $C_7$–$C_{12}$-aralkyl or $C_7$–$C_{12}$-alkylphenyl, or a saturated, unsaturated, or aromatic 5- or 6-membered heterocyclic with 1 or 2 hetero atoms selected from the group consisting of nitrogen, oxygen and sulfur, or a counter-ion of the corresponding alcoholate or thiolate or, if X is sulfur, $R^3$ is hydrogen, and X is oxygen or sulfur, and the stated organic radicals may furthermore carry substituents which are inert under the reaction conditions, which process comprises:

reacting a dinitroimidazole of the formula

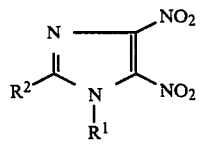

with an alcohol or thiol of the formula

in a solvent or diluent selected from the group consisting of water, water-miscible inert organic solvents and mixtures thereof, at a pH of from 4 to 16 and at a temperature of 0° to 150° C.

2. A process as claimed in claim 1, wherein $R^{11}$ of the formulas (I) and (II) is methyl or benzyl.

3. A process as claimed in claim 1, wherein $R^2$ of the formulas (I) and (II) is hydrogen or methyl.

4. A process as claimed in claim 1, wherein the solvents or diluents used are water and/or $C_1$–$C_4$-alcohols.

5. A process as claimed in claim 1, wherein the reaction is carried out at a pH of from 6 to 14.

6. A process as claimed in claim 1, wherein the pH is obtained by adding a base.

7. A process as claimed in claim 1, wherein an alkali metal ion, alkaline earth metal ion, ammonium ion or trialkylammonium ion is present as the counter-ion of the alcoholate or thiolate.

8. A process as claimed in claim 1, wherein the base used is ammonia, a tertiary amine or a carbonate, bicarbonate, hydride or hydroxide of an alkali metal or alkaline earth metal.

9. A process as claimed in claim 1, wherein from 1 to 20 moles of base are used per mole of dinitroimidazole II.

10. A process as claimed in claim 1, wherein from 1 to 5 moles of a compound III are used per mole of dinitroimidazole II.

* * * * *

UNITED STATES PATENT AND TRADEMARK OFFICE
CERTIFICATE OF CORRECTION

PATENT NO. : 4,900,825
DATED : February 13, 1990
INVENTOR(S) : Hermann Koehler and Toni Dockner It is certified that error appears in the above-identified patent and that said Letters Patent is hereby corrected as shown below:

Claim 2, column 10, line 36,
  change "$R^{11}$" to --$R^1$--.

Signed and Sealed this

Ninth Day of July, 1991

Attest:

HARRY F. MANBECK, JR.

Attesting Officer

Commissioner of Patents and Trademarks